United States Patent [19]
Thomas

[11] 3,953,616
[45] Apr. 27, 1976

[54] ORGANIC ACID DERIVATIVES

[75] Inventor: Paul D. Thomas, Groton, Conn.

[73] Assignee: Pfizer Inc., New York, N.Y.

[22] Filed: July 25, 1973

[21] Appl. No.: 382,394

Related U.S. Application Data

[60] Division of Ser. No. 805,020, March 6, 1969, which is a continuation of Ser. No. 446,429, April 7, 1965, abandoned, and Ser. No. 661,221, Aug. 17, 1967, abandoned, which is a continuation-in-part of Ser. No. 391,080, Aug. 21, 1964, Pat. No. 3,343,964, which is a continuation-in-part of Ser. No. 306,277, Sept. 3, 1963, abandoned.

[52] U.S. Cl. ............................................. 426/637
[51] Int. Cl.² ............................................ A23K 1/00
[58] Field of Search ........... 426/464, 473, 194, 321, 426/637; 127/71; 424/31; 260/485

[56] References Cited
UNITED STATES PATENTS

| 3,054,683 | 5/1960 | Hendel | 426/473 |
| 3,145,109 | 8/1964 | Howard | 426/194 |

Primary Examiner—Wilbur L. Bascomb, Jr.
Assistant Examiner—Martin G. Mullen
Attorney, Agent, or Firm—Connolly and Hutz

[57] ABSTRACT

This invention relates to certain novel starch compositions. More particularly, it is concerned with certain useful salts of various half-acid organic esters which have been found to be of value in industry when used in conjunction with starch. The invention includes the use of these salts as well as the compositions containing them within its scope.

5 Claims, No Drawings

ORGANIC ACID DERIVATIVES

CROSS-REFERENCE TO RELATED APPLICATIONS

This present application is a divisional application of my copending application Ser. No. 805,020, filed Mar 6, 1969, which in turn is a continuation of my patent applications, Ser. No. 446,429, filed Apr. 7, 1965 and now abandoned, and Ser. No. 661,221, filed Aug. 17, 1967 and now abandoned, the latter of which is a continuation-in-part of my patent application, Ser. No. 391,080, filed Aug. 21, 1964, now U.S. Pat. No. 3,343,964, which in turn was a continuation-in-part of my earlier application, Ser. No. 306,277, filed Sept. 3, 1963 and now abandoned.

In one embodiment, the invention described in this application relates to certain novel flour or farinaceous compositions. More particularly, it is concerned with various higher alkyl succinate salts which have been found to be of value in the food industry when used in conjunction with flour. The invention includes the use of these compounds as well as the flour compositions containing them within its scope.

In the baking art, natural variations in flour characteristics have been the source of a continuous problem or obstacle to the workers in this field even when flours of the highest quality grade are carefully selected. Long a problem in conventional baking, this matter has now been further accentuated in continuous bread processing. In accordance with the present invention, on the other hand, the compounds disclosed and used herein help to even out variations in flour characteristics in view of the marked dough strengthening properties which they exhibit. As a result, greater tolerances are now provided in the mixing, fermenting and machining operations, causing a baked product to be obtained with improved grain and texture as well as over-all quality. In addition, the rate of crumb firming is retarded and there is also no need to use such emulsifiers as mono-diglycerides and calcium stearyl-2-lactylate, etc.

The compounds which are included within the purview of this invention are all selected from the group consisting of the monoalkali and alkaline-earth metal salts of maleic and fumaric half-acid esters and higher alkyl succinates having the following formulae:

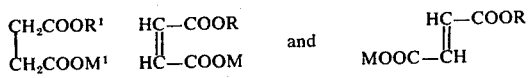

wherein R is an alkyl radical of from 14 to 18 carbon atoms, $R^1$ is an alkyl radical of from 14 to 20 carbon atoms, M is a metallic cation selected from the group consisting of sodium, potassium, calcium and magnesium and $M^1$ is a metallic cation selected from the group consisting of sodium, potassium and calcium. Typical member compounds of this series include sodium monostearyl fumarate, calcium monostearyl fumarate, sodium monostearyl maleate, sodium monocetyl fumarate, potassium monostearyl fumarate, magnesium monotetradecyl maleate, calcium monocetyl fumarate, sodium cetyl succinate, sodium stearyl succinate, potassium stearyl succinate, sodium tetradecyl succinate, calcium cetyl succinate and potassium eicosyl succinate and the like. All these compounds are useful as bread softening agents in view of their ability to retard the firming of bread when incorporated into the dough of the baking mix prior to baking.

The process employed for preparing the novel compounds of this invention involves the following steps starting from maleic anhydride: (1) the formation of the monoalkyl acid maleate ester from the aforementioned anhydride by treatment of the latter with an equivalent amount of the desired alkanol having the requisite number of carbon atoms; (2) the production of the sodium, potassium, calcium or magnesium salt of the aforementioned half-acid ester by conventional procedure; and (3) the conversion or isomerization of said salt or of the half-acid ester itself to the corresponding fumarate compound by standard catalytic means. Needless to say, if the half-acid maleate ester rather than the salt itself is converted to the fumarate compound, then the desired salt compounds can be subsequently obtained therefrom, i.e., from the corresponding half-acid fumarate ester, in accordance with the usual conventional procedure.

Alternatively, it is also possible to prepare the desired compounds of this invention from the appropriate dicarboxylic acid starting materials by simply using a method which involves classical esterification and selective monosaponification procedures. More specifically, the two steps of this method involve first treating the organic acid with at least a dimolar amount of the desired alkanol to form the corresponding diester, and then subjecting the dialkyl ester so formed to the selective action of one equivalent amount of sodium, potassium or calcium hydroxide, as the case may be, in an aqueous system to yield the corresponding salt of the half-acid ester. Needless to say, in the case of both routes, if the alkali metal salt is the compound which is formed first, then the corresponding calcium or magnesium compound may be subsequently prepared therefrom by means of a simple metathetical reaction.

In connection with a more detailed consideration of one of the preferred routes of synthesis for these compounds, maleic anhydride is first reacted with the desired higher alkanol of choice in the presence of a reaction-inert organic solvent medium under substantially anhydrous conditions. This usually entails carrying out the reaction in an aromatic hydrocarbon solvent such as benzene, toluene, xylene, and the like, and employing a nitrogen atmosphere or similar conditions in order to ensure completeness of reaction. In general, only equimolar amounts of reactant and reagent need be employed here and the reaction is ordinarily conducted at the reflux temperature of the reaction mixture for the sake of both time and convenience, although any temperature in the range of from about 40°C. up to about the boiling point of the solvent will be found to be most satisfactory for the purposes at hand (this will set the upper limit of the temperature range in the neighborhood of 140°C. when xylene is used). A time period of from about one-half to about 10 hours will ordinarily suffice under these conditions. Upon cooling the spent reaction mixture down to room temperature, crystals of the desired half-acid ester of maleic acid soon separate therefrom and they can subsequently be collected by such means as suction filtration and the like.

The conversion or isomerization of the half-acid ester of maleic acid thus produced to the corresponding fumarate compound is then effected by any number of standard procedures using a halogen as catalyst and preferably by the method which involves treating said maleate ester with bromine as catalyst in the presence of a minor amount of 2,2-azabis(2'-methylpropionitrile). This particular reaction is ordinarily conducted in a halogenated hydrocarbon solvent such as methylene chloride, ethylene dichloride, trichlorethylene, chloroform, S-tetrachlorethane and carbon tetrachloride, etc., and generally, at the reflux temperature of the mixture, although any temperature in the range of from about 30°C. up to about the boiling point of the solvent will suffice (this will set the upper limit of the temperature range in the neighborhood of 145°C. when S-tetrachlorethane is used). A time period of from about one-half to about 7.5 hours will oridnarily be most satisfactory for the purposes at hand. Upon completion of this step, the desired monoalkyl acid fumarate ester is recovered from the reaction mixture in the form of a crystalline precipitate.

Finally, the production of the desired monoalkali and calcium and magnesium salts of these compounds from the aforementioned half-acid esters themselves can then be effected by any number of conventional procedures in the art using first the desired alkali metal or calcium hydroxide as reagent in an aqueous system. In practice, it is preferable to employ an aqueous alcoholic or aqueous acetone solution of the half-acid ester compound containing an equivalent amount in moles of the appropriate metal hydroxide. The desired salt soon precipitates from solution almost immediately upon completion of this step. Other solvents which may be used in place of acetone in this connection include other lower alkyl ketones such as methyl ethyl ketone, diethyl ketone, methyl isoamyl ketone, and the like, while suitable alcohol solvents include such lower alkanols as methanol, ethanol, isopropanol, tertiary-butanol and tertiary-amyl alcohol, etc. The calcium monoalkyl maleates and/or fumarates may, alternatively, also be prepared from the corresponding monoalkali compounds thus formed, as are the magnesium compounds, by means of a simple metathetical reaction involving the use of an appropriate alkaline-earth metal halide, such as calcium chloride or magnesium bromide, in an aqueous system to yield the desired calcium or magnesium salt, as the case may be.

The process employed for preparing the useful compounds of this invention involves the following main two reaction steps starting from succinic anhydride, viz., (1) the formation of the desired monoalkyl acid succinate ester from the aforementioned anhydride by treatment of the latter compound with an equivalent amount in moles of the desired alkanol of choice having the requisite number of carbon atoms, and (2) the subsequent production of the corresponding sodium, potassium and calcium salts of this compound, i.e., of the aforementioned half-acid ester, by means of conventional salt-formation treatment.

In connection with a somewhat more detailed consideration of the preferred method of synthesis for the salt compounds themselves, a corresponding higher alkyl half-acid ester of the type referred to above is contacted with either sodium, potassium or calcium hydroxide, as the case may be, in accordance with conventional procedure in an aqueous solvent system. In practice, it is preferable to employ an aqueous alcohol or aqueous acetone solution of the half-acid ester compound containing an equivalent amount in moles of the appropriate metal hydroxide of choice. The desired salt soon precipitates from solution almost immediately upon completion of this step. Other solvents which may be used here in place of acetone include other lower alkyl ketones like methyl ethyl ketone, diethyl ketone and methyl isoamyl ketone, while suitable alcohols for use in this connection include lower alkanols such as methanol, ethanol, isopropanol and n-butanol, for example. Further, the desired calcium salts of this invention may also be prepared by an alternative route involving a simple metathetical reaction starting from the corresponding monoalkali compounds and using a calcium halide salt, such as calcium chloride or bromide, to effect said conversion.

As previously indicated, the succinate compounds of this invention are all useful as bread softening agents to prevent staling, in addition to being useful for improving the condition of the dough as well. In carrying out the baking process proper, only minor proportionate amounts of the instantly claimed compounds need be used in the dough batch or baking mix in order to achieve effective results in this connection. For instance, concentrations as low as 0.1% by weight of the compound, based on the weight of the flour, have been found to be effective and, in general, one need only employ these compounds at levels that are in the range of from about 0.1% up to about 3% by weight of the softening agent in order for highly satisfactory results to be achieved. Moreover, the sodium, potassium and calcium salts of the higher alkyl acid succinates of this invention accomplish their useful firmness-retarding activity in bread without causing any adverse side effects to occur, i.e., they do not adversely affect the crumb size, grain, crust, color, texture, specific volume or flavor of the finished bread products when the latter are baked under normal, standard conditions. The bread-softening activity of these compounds is also surprising when one considers that the corresponding higher alkyl acid succinates from which they are derived lack this activity to a substantial degree.

Additionally, the compounds of this invention impart improved qualities in general, including anti-staling properties, to such baked products as rolls, doughnuts, biscuits, cakes, pastries and the like, as well as bread, when added to the dough in the quantities previously indicated. For instance, among the specific advantages which have been realized by their use in this manner with respect to the yeast-leavened products are: (1) retardation of crumb firming; (2) improved dough handling characteristics; (3) improved ingredient and processing tolerances; (4) reduction in proof time; and (5) improved physical characteristics, such as the grain, texture and volume of the finished baked goods. Furthermore, chemically-leavened baked products also benefit equally as well by the use of these compounds in the baking dough or batter prior to baking in the same manner as before. Thus, for example, improved batter and/or dough handling characteristics have resulted, as well as improved finished goods properties and firmness development with respect to the crumb quality. In almost every case, the most outstanding compound of all those tested and the one which is, therefore, the most preferred member of this invention is sodium cetyl succinate.

Moreover, the compounds of the present invention are useful in farinaceous starch products in the food field in general. For instance, they have been found to impart properties to the quality and texture of such products as grain cereals, macaroni and the like, if said products are first treated with these compounds just prior to cooking. The advantages afforded by the use of these compounds in this manner, i.e., as applied to starch-based foods, are manifold: for instance, they prevent undesirable stickiness and pastiness from occurring in said products, thereby resulting in increased production advantages as well as in increased consumer appeal of the finished product. Examples of practical illustrations of the present invention include the use of these compounds in such starch-based foods as instant potato flakes or granules, macaroni products and spaghetti, hot breakfast food cereals, and the like, and starch-based pie-fillings and dessert puddings, as well as in dehydrated creamed soups and various rice products, etc. In each case, the starch-containing product is improved as to both its quality and texture in view of the ability of these compounds to reduce the inherent stickiness and pastiness of the starch-containing food material as previously indicated.

In accordance with the process of this invention for effecting said improvement in starch-based foods, a starch-containing or starch-based food material is first treated with a relatively minor amount of the organic compound heretofore mentioned just prior to the cooking step. In general, all that is usually necessary is to use at least about 0.1% by weight of the compound based on the total weight of the starch-based food material. In some instances, even less than this amount may be effective, but it is generally not advisable to go below the aforementioned lower limit. The upper limit can be preferably set at about 4% (or 3% in the case of the succinates) although this is not really critical, except in the case of potatoes, and amounts as high as 6% by weight have been used. Nevertheless, there is no real appreciable advantage to be gained in exceeding the aforementioned 4% weight limit and in the case of potatoes, no more than about 2% by weight of the compound should be used. The important point to remember is that the addition and subsequent mixing steps must be accomplished prior to the cooking of the starch-based food material. Of especial interest in this connection is the fact that sodium monostearyl fumarate and sodium cetyl succinate have been found to be particularly valuable as agents for improving the quality and texture of macaroni products. For instance, these compounds have been found to increase firmness of the food product itself, as well as to improve its tolerance to overcooking and prevent clinging and stickiness of the individual noodle strands from occurring. These improved properties of the finished food material are of especial value in those cases where the macaroni product is intended for use in the canning industries and in the institutional trades, such as mass feeding establishments, etc.

In addition, sodium monostearyl fumarate and the related compounds of this invention are also of value as conditioning agents for use in dehydrated potatoes that are ultimately to be reconstituted with water. In this way, the effect achieved is one of greater tolerance in the reconstitution step, thereby resulting in a less pasty, drier-appearing finished product as compared to the control. In this connection, it is preferable to add the conditioning agent of this invention to the dehydrated potatoes in comminuted form during processing, i.e., before exposure to the adverse conditions which tend to rupture the starch granules. In general, concentration levels ranging from about 0.1% to about 2% by weight, based on dried potato weight, are sufficient in order to achieve the aforesaid effect, which amounts to the product having the advantages of being less watery and less gummy and having an improved body texture.

Additional industrial applications for these compounds lie in the non-food area where starch is also involved as a key ingredient. For instance, these compounds allow for a higher starch solids concentration at useful viscosity ranges or conversely, provide lower viscosities at equivalent starch solids concentrations. They also allow for a facilitation in the handling of starch pastes and, for the stabilization of same with respect to viscosity and uniformity, particularly at elevated temperatures. The tendency toward solids deposition from the pastes is also reduced, i.e., retrogradation is inhibited. All these properties are of value in using the present compounds in conjunction with starch to prepare pharmaceutical tablets, gums, jellies, confections and the like, as well as in paper and textile sizing, and starch manufacture. With regard to those industrial applications that are not intended primarily for oral human consumption as their end use, sodium monostearyl maleate is the preferred compound of choice in view of the economics involved. However, other preferred compounds which may be used for these purposes include sodium monocetyl fumarate, sodium monocetyl maleate, and sodium monostearyl fumarate.

More specifically, the compounds of this invention have been found to inhibit gelation in starches when they are added to the pastes containing same at low temperatures, i.e., just prior to gelation. This addition must be made at, at least, about the 0.1% concentration level, based on starch. On the other hand, when added to the pastes that have already gelled, these compounds cause an increase in viscosity, with the latter effect being particularly true in wheat, corn and rice starch. For instance, when sodium monostearyl fumarate was added to the initial paste at room temperature, it was found to inhibit starch granule swelling in the paste as evidenced by lowered paste viscosities. However, when added to a gel that had already reached maximum viscosity, its effect was to increase the viscosity beyond that point, i.e., above that of the control maximum. As previously indicated, the gelation effect was quite dramatic in the case of wheat starch, corn starch and rice starch when sodium monostearyl fumarate was added to their pastes at room temperature at a 2% concentration level based on starch weight, followed by a heating cycle. Furthermore, in flour all these compounds exert an almost equal but yet different effect on both the starch and gluten fractions. For instance, starch granule swelling is retarded same as before, while the gluten structure is strengthened. This effect on gluten takes place at non-elevated temperatures, since in doughs prepared at room temperature, the gluten strengthening effect was observed. On the other hand, the effect on starch appears to take place only at higher temperatures, i.e., at temperatures above about 50°C.

In summary, therefore, the present invention is concerned with compositions comprising starch and at least about 0.1% by weight based on said starch of a substance selected from the group consisting of the sodium, potassium, calcium and magnesium salts of monoalkyl fumarates and maleates containing from about 14 to 18 carbon atoms in the alkyl group. These compositions have film-forming, thickening and starch-adhesive properties. More particularly, it is concerned with food compositions comprising an edible starch and from about 0.1 to 4% by weight based on said starch of a substance as hereinbefore described. The preferred compounds for the food compositions are the fumarates of from 16 to 18 carbon atoms in the alkyl group and especially, sodium monostearyl fumarate and sodium monocetyl fumarate. The starch present in these compositions can be in the form of a cereal grain like wheat, rice, maize, oats and barley, etc. In addition, it is also concerned with improved potato compositions comprising these compounds and the instant dehydrated potato in comminuted form, whereby the compound serves as a conditioning agent therefor in connection with the reconstitution step with water, as previously described. In this instance, the compound is present at a level ranging from about 0.1% to about 2% by weight, based on the weight of the dried potato.

Moreover, the invention also includes within its scope the method of improving the properties of aqueous starch dispersions, which comprises the step of incorporating therein at least about 0.1% by weight based on said starch of the substance heretofore mentioned, i.e., a substance selected from the group consisting of the sodium, potassium, calcium and magnesium salts of monoalkyl fumarates and maleates containing from about 14 to 18 carbon atoms in the alkyl group. More particularly, it is concerned with the method of reducing stickiness in water-containing cereal grain products by incorporating these compounds within said compositions at concentration levels ranging from about 0.1 to about 4% by weight based on the weight of said cereal grain. It is also concerned with the method of improving potato compositions adapted for reconstitution with water by incorporating the compounds of the present invention therein at levels ranging from about 0.1% to about 2% by weight based on the weight of the dried potato. As previously indicated, the preferred compounds for these edible compositions are the fumarates containing from 16 to 18 carbon atoms in the alkyl group.

The present invention is likewise concerned with farinaceous compositions comprising flour and at least about 0.1% by weight based on said flour of a compound selected from the group consisting of the sodium, potassium and calcium salts of higher alkyl acid succinates containing from 14 to 20 carbon atoms in the alkyl group. More particularly, it is concerned with farinaceous compositions comprising the flour and from between about 0.1 to about 3% by weight based on said flour of a compound of the type as hereinbefore described. The preferred compounds for these food compositions are the higher alkyl acid succinate salts of from 16 to 18 carbon atoms in the alkyl group and especially, sodium cetyl succinate and sodium stearyl succinate. The flour present in these compositions can preferably be a wheat flour of either the bleached or unbleached variety and it is normally present in intimate admixture with the compound of choice. Needless to say, the baked leavened dough products so produced from these compositions also lie within the scope of this invention, as do aqueous farinaceous compositions containing these compounds at the aforementioned weight levels.

Moreover, the invention also includes within its scope the method of improving the properties of aqueous farinaceous dispersions, which comprises the step of incorporating therein at least about 0.1% by weight, based on the weight of the flour, of the compound heretofore mentioned, i.e., one selected from the group consisting of higher alkyl acid succinate salts containing from 14 to 20 carbon atoms in the alkyl group. More particularly, it is concerned with the method of retarding the staling rate of various baked leavened dough products. This is accomplished by incorporating the compounds of the present invention in said compositions at concentration levels ranging from between about 0.1 to about 3% by weight, based on the weight of the flour contained in said dough. As previously mentioned, the preferred compounds for these edible starch compositions are the higher alkyl acid succinate salts containing from 16 to 18 carbon atoms in the alkyl group.

This invention is further illustrated by the following examples, which are not to be construed in any way or manner as imposing limitations upon the scope thereof. On the contrary, it is to be clearly understood that resort may be had to various other embodiments, modifications and equivalents thereof which readily suggest themselves to those skilled in the art without departing from the spirit of the present invention and/or the scope of the appended claims.

EXAMPLE I

In a 2000 ml. three-necked, round-bottomed flask equipped with mechanical stirrer, thermometer, nitrogen-capillary tube and reflux condenser fitted with a drying tube, there were placed 196 g. (2.0 moles) of maleic anhydride and 540 g. (2.0 moles) of stearyl alcohol suspended in 1000 ml. of toluene. The resulting mixture was then warmed to effect solution and refluxed for two hours thereafter while under a nitrogen atmosphere. The resulting clear, light yellow solution was then cooled in an ice-water bath, whereupon colorless crystals of monostearyl maleate soon precipitated. The crystals so obtained were subsequently collected on a filter funnel, washed with toluene and then dried in a vacuum oven at 50°C. In this manner, there were obtained 574.3 g. of product, melting at 80°–81°C., in the form of brilliant colorless plates. A second crop of crystals was obtained by merely concentrating and cooling the mother liquors to afford 56.1 g. of additional product melting at 78°C. The combined yield of monostearyl maleate amounted to 86% of the theoretical.

EXAMPLE II

The procedure described in Example I is followed to prepare other maleate monoester compounds by merely employing the appropriate aliphatic alcohol in place of stearyl alcohol on an equivalent molar basis in each case. The compounds specifically prepared by this method are monocetyl maleate and monotetradecyl maleate, respectively.

EXAMPLE III

In a 2000 ml. three-necked, round bottomed flask equipped with stirrer, dropping funnel and reflux condenser fitted with a drying tube, there were placed 600 g. of monostearyl maleate dissolved in 1300 ml. of warm carbon tetrachloride. Six grams of 2,2''-azabis (2'-methylpropionitrile) were then added and the resulting solution was heated to reflux, while 5.2 g. of bromine in 400 ml. of carbon tetrachloride were subsequently added thereto from a dropping funnel at such a rate that 14 ml. of added solution were consumed per minute. This addition was completed during the course of a 30-minute period. At the end of this time, the reaction mixture was refluxed for an additional 45 minutes and then cooled to room temperature. The white precipitate which formed at this point was subsequently collected by means of vacuum filtration, washed with carbon tetrachloride on the filter funnel and dried in vacuo at 45°C. In this manner, there were obtained 508.5 g. (85%) of monostearyl fumarate, m.p. 93°–94°C.

Anal. Calcd. for $C_{22}H_{40}O_4$: saponification no., 184; neut. equiv., 368. Found: saponification no., 182; neut. equiv., 368.

EXAMPLE IV

The procedure described in Example II is followed to prepare other fumarate monoesters by merely employing the appropriate maleate monoester (these are reported in Example II) in each case as starting material for the reaction in place of the monostearyl maleate. The compounds specifically prepared in this manner are monocetyl fumarate and monotetradecyl fumarate, respectively.

EXAMPLE V

Four-hundred and forty grams (440 g., 1.20 moles) of monostearyl fumarate were dissolved in 2.5 liters of acetone in a four-liter beaker with warming and stirring. The resulting solution was then cooled to 45°–50°C. and a solution of 49.5 g. (1.20 moles) of sodium hydroxide in 450 ml. of water was slowly added thereto. Upon the completion of this step, the reaction mixture was cooled in an ice-water bath to 10°C., filtered and the resulting filter cake washed with acetone and dried in a vacuum oven at 50°C. In this manner, there was obtained 474 g. (99%) of sodium monostearyl fumarate.

Anal. Calcd. for $C_{22}H_{39}O_4Na$; C, 67.66; H, 10.01; saponification no., 391 Found: C, 67.25; H, 9.91; saponification no., 397.

EXAMPLE VI

The procedure described in Example V is followed to prepare other monosodium salts, viz., the salts of those acids previously reported in Examples I–II and IV. In each and every case, equimolar quantities of reactants and reagents are employed as in Example V. In this manner, the following compounds are obtained:
sodium monocetyl maleate
sodium monocetyl fumarate
sodium monostearyl maleate
sodium monotetradecyl maleate
sodium monotetradecyl fumarate

EXAMPLE VII

The procedure described in Example V is followed to prepare the potassium and calcium salts of the acids previously reported in Examples I–III and IV. This is accomplished by employing potassium and calcium hydroxide, respectively, in place of sodium hydroxide on an equivalent molar basis in this reaction. The compounds obtained in this manner are listed below as follows:
potassium monostearyl maleate
potassium monostearyl fumarate
calcium monostearyl maleate
calcium monostearyl fumarate
potassium monocetyl maleate
potassium monocetyl fumarate
calcium monocetyl maleate
calcium monocetyl fumarate
potassium monotetradecyl maleate
potassium monotetradecyl fumarate
calcium monotetradecyl maleate
calcium monotetradecyl fumarate

EXAMPLE VIII

Two-hundred grams (200 g., 0.511 mole) of sodium monostearyl fumarate were placed in 2.5 liters of water in a four-liter beaker. The resulting slurry was then heated on the steam bath until the sodium salt had thoroughly dissolved. To the resulting hot aqueous solution, there was then added an aqueous solution consisting of 35 g. of anhydrous calcium chloride dissolved in 250 ml. of water. The resulting precipitate was filtered while hot, washed with cold water and then with acetone, and allowed to dry in the vacuum oven at 50°C. In this manner, there were obtained 191.2g.(96%) of calcium monostearyl fumarate.

Anal. Calcd. for $C_{22}H_{39}O_4.Ca/2$: C, 68.17; H, 10.14; Ca, 5.18. Found: C, 67.80; H, 9.97; Ca, 5.35.

EXAMPLE IX

The procedure described in Example VIII is followed except that magnesium bromide is used in place of calcium chloride as the reagent of choice on the same molar basis to afford the corresponding magnesium salt, viz., magnesium monostearyl fumarate.

In like manner, other alkali metal compounds such as those reported in Example VI–VIII can be used instead of sodium monostearyl fumarate to react with the appropriate alkaline-erth metal salt and yield the corresponding calcium or magnesium monoalkyl fumarate and/or maleate, as the case may be. For instance, potassium monotetradecyl maleate reacts with calcium chloride on this basis to give calcium monotetradecyl maleate, while sodium monocetyl fumarate and magnesium chloride react to yield magnesium monocetyl fumarate. Other compounds obtained in this manner are listed below as follows:
calcium monocetyl maleate
calcium monocetyl fumarate
magnesium monocetyl maleate
calcium monostearyl maleate
magnesium monostearyl maleate
calcium monotetradecyl fumarate
magnesium monotetradecyl maleate
magnesium monotetradecyl fumarate

EXAMPLE X

Eight grams of corn (maize) starch derived from a cereal grain and 200 ml. of water were mixed together in the following manner: a small amount of water was first added to the dry material sufficient to make a paste and then the remainder of the water was added to the paste followed by the subsequent heating of the mixture to the boiling point. After boiling for one-half minute and then allowing the mixture to stand overnight for about 16 hours at ambient temperatures, there was obtained a semi-solid gel. When the aforementioned test was repeated again only this time using 0.16 g. (2.0%) of sodium monostearyl fumarate together with the corn starch in a dry mixture, there was obtained a fluid material having the approximate consistency of unbeaten egg white. Additionally, the fluid material had almost no surface skin on top, unlike the control which did have a heavy surface skin or film in this area.

After holding both samples in hot water for one hour, the control had completely gelled while the sample containing the sodium monostearyl fumarate was still a fluid liquid. The latter was then boiled for 10 minutes and although it became somewhat slightly thicker (due to water evaporation), it still did not form a gel.

EXAMPLE XI

The procedure described in the previous example is repeated using the other fumarate and maleate compounds described in Example VI–IX. In each and every case, the results obtained are substantially the same as those reported in Example X for sodium monostearyl fumarate at the 2.0% level.

In like manner, the use of sodium monostearyl fumarate at the 0.1% concentration level, based on the weight of the starch, and at the 4.0% concentration level also affords similar results, as does any of the compounds listed in Examples VI–IX, like sodium monocetyl fumarate and sodium monotetradecyl fumarate, for instance.

EXAMPLE XII

The procedure described in Examples X and XI is followed using other starches in place of corn starch. For instance, the following starches have been found applicable under the present circumstances: wheat starch, rice starch, oat starch and barley starch. In each instance, the results obtained are similar to those reported in Examples X and XI.

EXAMPLE XIII

A 5% paste of corn starch (5 g. in sufficient water to total 100 g. of mixture) was prepared having a maximum viscosity reading of 130 B.U. (Brabender Units) at 95°C. when tested in a Brabender Visco Amylograph for these purposes. On holding the paste at 95°C. for 20 minutes and subsequently cooling down to room temperature (~25°C.), there was obtained a solid plastic gel.

When these two steps were repeated with a similar starch paste but one containing 2% sodium monostearyl fumarate, based on the weight of the corn starch, added at the point of maximum viscosity of the control, there was obtained a product having the maximum viscosity reading of 160 B.U. at 95°C. When this paste containing the added organic compound was cooled down to room temperature after having been held at 95°C. for a 20 minute period, there was obtained a fluid dispersion (200 B.U. at 25°C.) which poured readily. Upon evaporation of this dispersion to dryness while under reduced pressure, there was obtained an amorphous material which could be reconstituted to its original consistency by warming to 50°C.

1% Sodium monostearyl fumarate, under the same circumstances, also gave similar results although the cooled paste containing same was somewhat more viscous than the finished product discussed above. Nevertheless, it was far superior to the control in this respect and, in addition, it could still be poured with only slight difficulty.

EXAMPLE XIV

A corn starch paste (~8%) was prepared by blending 40 g. of said material (which is actually derived from a cereal grain) with 450 g. of water. When 2% sodium monostearyl fumarate, based on the weight of the starch, was added to the initial starch paste mixture at room temperture (25°C.) and heated to 95°C., there was obtained a noticeable inhibition of granule swelling over the control. The effect of adding 2% sodium monostearyl fumarate to the paste at the temperature of maximum viscosity (92.5°C.), however, resulted in an increase in viscosity over that of the control which amounted to about 330 Brabender Units (B.U.) at the end of the run (20 minutes at 92.5°C.).

EXAMPLE XV

The procedure described in the previous two examples was repeated with rice starch (also derived from a cereal grain) instead of corn starch. The viscosity changes obtained in this instance were similar to those reported previously in Examples XIII – XIV.

EXAMPLE XVI

The procedure described in Examples XIII – XIV was repeated only this time using wheat starch as the substrate of choice. The gelation inhibition with 10% wheat starch (50 g. in 450 g. of water) at three different sodium monostearyl fumarate levels, based on starch weight, was studied. At the 2% level, it was found that the viscosity of the treated initial starch paste at room temperature did not increase (no swelling of starch granules), even after holding at 95°C. for more than 1 hour. 1% Sodium monostearyl fumarate, on the other hand, caused no swelling of starch granules to occur until a temperature of 95°C. was reached and after holding at that point for 20 minutes, the viscosity increased to 180 B. U. With 0.5% sodium monostearyl fumarate, the viscosity was stabilized at 520–540 B.U. during the holding period at 95°C., although starch granule swelling was inhibited before that point.

When sodium monostearyl fumarate was added to a 10% wheat starch paste at 0.5, 1.0 and 2.0% levels at the temperature of maximum viscosity, the viscosity was found to increase in every instance. This increase was also found to be proportional to the organic compound concentration within this range. For instance, with 2% of sodium monostearyl fumarate added in this manner, the viscosity increased by 1000 B.U. after two minutes, and was 750 B.U. higher than the control maximum after 20 minutes.

EXAMPLE XVII

The procedure described in the previous example was followed to compare the effect of increasing the weight of wheat starch levels while maintaining the sodium monostearyl fumarate concentration constant at the 2% level, based on the weight of the starch present. It was found that with an 11.8% starch concentration (60 g. in 450 g. water), granule swelling was still drastically inhibited although some increase in the viscosity was noted after 60 minutes at 95°C. In the case of wheat starch at the 13.4% concentration level (70 g.), granule swelling was still inhibited and the decrease in viscosity as compared to the control was still significant. At a 15.1% concentration of wheat starch (80 g.), swelling was restricted to a significant degree although the viscosity increased quite rapidly on holding at 95°C. for a slightly prolonged period of time.

EXAMPLE XVIII

The procedure described in Examples XIII – XVII is repeated using the other fumarate and maleate compounds described previously in Examples VI – IX. In each and every case, the results obtained are substantially the same as those reported previously for sodium monostearyl fumarate as regards both the fluid dispersion (gelation inhibition) and starch thickening effect achieved with the starch-based compositions.

Additionally, these effects have also been achieved with the compounds of choice at concentration levels as low as 0.1%, based on the weight of the starch. In this respect, sodium monostearyl fumarate, calcium monostearyl fumarate, sodium monostearyl maleate, sodium monocetyl fumarate and sodium and potassium monotetradecyl maleate have all been found to be particularly effective. Furthermore, the starch compositions prepared by using these compounds at the aforementioned levels have all been found to be effective for use as industrial adhesive agents.

EXAMPLE XIX

The gluten fraction of wheat flour was separated from the starch fraction by means of a standard dough-washing procedure [see M. J. Wolf in "Metods in Carbohydrate Chemistry", Vol. IV, p. 6, Edited by R. L. Whistler, Academic Press, New York (1964)]. The gluten obtained from the dough was then examined and compared with that obtained from 1% sodium monostearyl fumarate (percentage based on flour) treated dough. In this manner, it was found that the gluten from the treated dough was more cohesive and resisted extension to a considerably greater degree than did the gluten obtained from the control dough. As a result, the strength of a moisture-containing wheat cereal flour composition is considerably enhanced by the use of sodium monostearyl fumarate due to the effect of this organic compound on the gluten fraction contained therein, i.e., dough improver properties result, caused in large part by the marked increase in strength of the gluten fraction as hereinbefore described.

EXAMPLE XX

The procedure described in Example XIII was repeated using rice flour paste (~8% concentration) as the substrate of choice. It was found that a markedly significant degree of granule swelling inhibition occurred when 2% sodium monostearyl fumarate (percentage based on flour) was used as compared to the control, as evidenced by the lower viscosities obtained throughout the Brabender Visco Amylograph run. The effects obtained with rice flour here are quite similar to those obtained rice starch, as reported elsewhere in the specification.

Tapioca flour was also tested in this manner and found to behave in a similar fashion when sodium monostearyl fumarate was added at the 2% level to a 6.25% paste at room temperature or at the temperature of maximum viscosity of the control.

EXAMPLE XXI

The procedure described in Example XIX is repeated using the other fumarate and maleate compounds described previously in Examples VI – IX. In each and every case, the results obtained are substantially the same as those reported previously with sodium monostearyl fumarate as regards the gluten-strengthening effect in moisture-containing cereal flour compositions.

In like manner, the use of any of these compounds at concentration levels ranging from 0.1% to 2% by weight, based on the flour, affords similar results. For instance, sodium monostearyl fumarate at the 0.1% level, sodium monostearyl maleate at the 0.5% level and sodium monocetyl fumarate at the 2% level have all been found to be effective.

EXAMPLE XXII

Sodium monostearyl fumarate was added to potato mash at a concentration level of 0.25% based on the weight of the dry solids present in the mixture. It was found that this step served to facilitate drying into granule form, as compared to the control. The reconstituted potato granules were then found to be not stiff and pasty, and they had a rapid release in the mouth. Sodium monostearyl fumarate at the 0.5% level also produced the same effect.

EXAMPLE XXIII

Eighty grams (80 g.) of unmodified corn starch was uniformly dispersed in cold water and the resulting mixture adjusted to an 8% (w./w.) concentration level. It was then heated to 95°C. on a steam bath and after heating for 20 minutes at that point, 1.6 g. of sodium monostearyl fumarate (2% based on the starch) dissolved in a minimum amount of hot water, was added to the mixture uniformly. The resulting starch paste was then heated to 95°C. for an additional 10 minutes. A portion of this paste was then withdrawn and used to caste a film. The film was allowed to dry at 70°F. and 50% relative humidity. It was found on close examination that this film was considerably more transparent and pliable and more readily soluble in most solvents than a similar film prepared in exactly the same manner, but lacking the added organic compound.

EXAMPLE XXIV

The procedure described in Example XXIII is repeated using other fumarate and maleate compounds described in Example VI–IX. In each and every case, the results obtained are substantially similar to those reported previously with sodium monostearyl fumarate as regards the film-forming effect.

Additionally, this same effect is also achieved when all these compounds are individually employed at a concentration level of 0.1% instead of at 2% as in the preceding example.

EXAMPLE XXV

The procedure described in Example XXIII to prepare the starch pastes is repeated only this time the pastes were allowed to cool to room temperature (70°F.) and used to glue two strips (1 X 4 inches) of Kraft paper together by coating them with same at their 1 X 1 inch center portion. It was noted that the starch paste containing the sodium monostearyl fumarate was easier to apply and gave a smoother, more uniform coating than did the control paste. Furthermore, upon prolonged storage, the control paste underwent retrogradation and weeping, whereas the starch paste of the example remained smooth and uniform.

EXAMPLE XXVI

The starch pastes prepared in Example XXIII were used to size cotton yarn at 190°F. It was noted that the starch paste containing sodium monostearyl fumarate gave a more uniform coating and a more acceptable set of weaving efficiencies than die the control Furthermore, it was also more stable as a solution during the application step and showed no signs of skinning as did the control. The viscosity of the instant sizing composition also remained constant throughout the entire operation.

EXAMPLE XXVII

Sodium monostearyl fumarate at levels of 0.5%, 1.0% and 1.5%, based on dried potato weight, was added to finished dehydrated, instant potato flakes which contained no food emulsifier. This addition was accomplished by simply dry blending the two ingredients together in a twin-shell mixer. The samples were then rehydrated and cooked, and shortly thereafterwards evaluated by means of comparison with a negative control that contained no sodium monostearyl fumarate. It was found that the sodium monostearyl fumarate samples were less watery in appearance than the negative control, having improved body texture and less gumminess as well. Further, at the 0.5% level, sodium monostearyl fumarate significantly improved the texture, with additional benefits also being seen at the 1.0% level. Although sodium monostearyl fumarate was equally as good at 1.5%, there were no additional advantages to be found at this particular level other than the firmer, drier and less pasty characteristics referred to above, as compared to the negative control.

EXAMPLE XXVII

The procedure described in th previous example is repeated here except that calcium monostearyl fumarate is employed instead of sodium monostearyl fumarate, with comparable results also being obtained. In like manner, sodium monocetyl fumarate, potassium monocetyl fumarate, calcium monocetyl fumarate, magnesium monocetyl fumarate, sodium monostearyl maleate, potassium monostearyl fumarate and magnesium monostearyl fumarate, as well as the other salt compounds of Examples VI – IX, can also each be used to replace sodium monostearyl fumarate and still achieve substantially similar results.

EXAMPLE XXIX

The procedure described in the preceding two examples is followed here except for the fact that concentration levels as low as 0.1% and as high as 2.0% by weight, based on dried potato weight, are employed in preparing the instant dehydrated potato compositions of the present invention. For instance, samples consisting of 0.1 g. of sodium monostearyl fumarate admixed with 100 g. of finished, instant dehydrated potato flakes in the manner of Example XXVII and 2.0 g. of calcium monostearyl fumarate admixed with 100 g. of the same said flakes (also in the manner of Example XXVII) are prepared and tested as described previously in the aforementioned example for sodium monostearyl fumarate 0.5%. In each and every case, the results obtained are almost substantially the same as those reported previously, with the results achieved at the lower level, particularly in the case of sodium monostearyl fumarate, being just somewhat less effective than is the situation at 0.5%.

EXAMPLE XXX

Sodium monostearyl fumarate (1.0 g.) is added to potato mash at a concentration level of 1% by weight based on the weight of the dry solids present in the mixture, i.e., 1.0 g. of compound per 100 g. of dry potatoes in comminuted form. This step served to facilitate drying the potatoes into granule form (as compared to the control) by reducing stickiness and pastiness and by minimizing the rupture of potato cells during processing. The potato granules so formed are then found to have a mealier, drier appearance as to body texture upon rehydration with water, as compared to the negative control. After prolonged heating on a steam table for three hours, the rehydrated potato granules containing sodium monostearyl fumarate are still found to be less sticky and pasty than the negative control.

In like manner, the use of calcium monostearyl fumarate, sodium monocetyl fumarate and sodium monostearyl maleate in place of sodium monostearyl fumarate in the above mixture, affords equally similar results in each case. When all these compounds are tested at the 0.25% concentration level, the effect achieved is still substantially the same.

EXAMPLE XXXI

In є 1000 ml. three-necked flask, equipped with mechanical stirrer, thermometer, nitrogen-capillary tube and reflux condenser, there were placed 50 g. (0.50 mole) of succinic anhydride, 121 g. (0.50 mole) or cetyl alcohol (hexadecanol) and 300 g. of toluene. The resulting mixture was first warmed to effect solution and then refluxed for 2 hours under a nitrogen atmosphere. The reaction mixture was then cooled down to room temperature (~25°C.) and the precipitate which formed was collected by means of suction filtration and dried in a vacuum oven at 40°C. The dried product amounted to 45.3 g. of colorless waxy crystals melting at 62–63°C. A second crop was then obtained by concentrating the filtrate to one-half volume and following the same procedure as before. In this manner, there was obtained a total yield of 67 g. of material (m.p. 58.5°–60°C.) which amounted to a 65% yield of monocetyl succinic acid.

EXAMPLE XXXII

The procedure described in Example XXXI was followed to prepare monostearyl succinic acid, starting from succinic anhydride but using stearyl alcohol in place of cetyl alcohol as reagent instead. In this particular case, 50 g. (0.50 mole) of succinic anhydride, 135 g. (0.50 mole) of stearyl alcohol and 300 g. of toluene were refluxed together for 1.5 hours and then allowed to cool to room temperature overnight. The precipitated crystals which formed were then collected on a filter funnel, washed with cold toluene and the resultant wet cake dried in a vacuum oven at 50°C. In this manner, there were obtained 142 g. of colorless plates melting at 73°–74°C. A second crop of crystals, melting at 72°–73°C., was also obtained. The combined yield, therefore, amounted to 165 g. (89%) of monostearyl succinic acid.

Anal. Calcd. for $C_{22}H_{42}O_4$: C, 71.30; H, 11.43. Found: C, 71.29; H, 11.22.

EXAMPLE XXXIII

The procedure described in Example XXXI is followed to prepare monotetradecyl succinic acid and monoeicosyl succinic acid, respectively, starting from succinic anhydride and employing an equimolar amount of the appropriate higher alkanol of choice in each instance, i.e., either tetradecanol or eicosanol, as the case may be.

EXAMPLE XXXIV

To a solution of 40 g. (0.117 mole) of monocetyl succinic acid in 200 ml. of acetone, there was slowly added a solution consisting of 4.8 g. of sodium hydroxide in 20 ml. of water. This was down with constant agitation of the reaction mixture throughout the addition step, with the temperature of same always being maintained below 40°C. until the addition of the alkali was complete. The resulting mixture was then cooled to 10°C. and filtered with suction to remove the precipitated solid salt. The filter cake was washed with acetone, sucked dry and then finally dried in a vacuum oven at 50°C. to afford 39.6 g. (93%) of sodium cetyl succinate in the form of a white powder. This salt was dispersible in water at the 0.1% weight-volume level at 25°C., while a 1% (W/V) dispersion of same was obtained at 50°C.

EXAMPLE XXXV

In a 2000 ml. Erlenmeyer flask, there were placed 150 g. of monostearyl succinic acid (acid value, 156.7) and 1200 ml. of acetone. This mixture was first warmed and stirred to effect solution and then cooled to 40°C., at which point 17.3 g. of sodium hydroxide in 100 ml. of water were slowly added. The addition step was accomplished with vigorous agitation of the mixture, while the temperature of the acetone solution was always maintained at 40°–43°C. throughout said step. The resulting reaction mixture was then stirred for a further 15 minutes, cooled down to 10°–15°C. and filtered with suction. The filter cake so obtained was washed twice with separate 100 ml. portions of cold acetone and sucked dry on the filter funnel. After drying the product in a vacuum oven at 50°C., it was found that a yield of 157.5 g. (98.5%) of sodium stearyl succinate was obtained. This particular salt, which was obtained in the form of a white powder, gave a 0.1% (W/V) aqueous dispersion at 25°C. and a 1% dispersion at 50°C.

EXAMPLE XXXVI

The procedure described in the preceding two examples is repeated again to prepare other sodium salts, viz., the sodium salts of those half-acid esters previously reported in Example XXXIII. In each instance, equimolar quantities of reactant and reagent are employed. The products specifically obtained are sodium tetradecyl succinate and sodium eicosyl succinate, respectively.

EXAMPLE XXXVII

The procedure described in Example XXXIV was followed to prepare potassium stearyl succinate, starting from 50 g. of monostearyl succinic acid in 400 ml. of acetone and using a solution of 9.24 g. of 85% potassium hydroxide in 35 ml. of water to effect said conversion. The yield of product obtained in this case was 54.3 g. (98%). The potassium salt, which was obtained in the form of a white powder, was found to be dispersible in water at the 1% level at 25°C. and at the 10% level at 50°C.

EXAMPLE XXXVIII

The procedure described in Example XXXVII is followed to prepare the potassium salts of the other half-acid esters reported in Examples XXXI and XXXIII, respectively. This is accomplished by using potassium hyroxide on the same molar basis as employed in the previous example for this reaction. In this particular case, the corresponding products obtained are potassium tetradecyl succinate, potassium cetyl succinate and potassium eicosyl succinate, respectively.

EXAMPLE XXXIX

The procedure described in Examples XXXIV – XXXV is followed here to prepare the calcium salts of the half-acid esters reported in Examples XXXI – XXXIII. This is accomplished by simply employing calcium hydroxide in place of sodium hydroxide on an equivalent molar basis in this same reaction. The compounds obtained in this manner are listed below as follows:
calcium tetradecyl succinate
calcium cetyl succinate
calcium stearyl succinate
calcium eicosyl succinate

EXAMPLE XL

Sodium cetyl succinate, prepared as described in Example XXXIV, was incorporated into a bread recipe having the following formula:

| 4-Hour Sponge | Grams |
|---|---|
| Flour | 1120 |
| Water | 615 |
| Yeast | 40 |
| Dough conditioner[1] | 8 |

| Dough Portion | Grams |
|---|---|
| Flour | 480 |
| Water | 417 |
| Sugar (granulated) | 128 |
| Salt | 34 |
| Calcium propionate | 66 |
| Milk powder | 48 |
| Lard | 40 |
| Sodium cetyl succinate | 8 |

[1]Potassium bromate, 0.3%; ammonium chloride, 9.7%; calcium sulfate, 25%; sodium chloride, 10%; and starch, 55%.

The ingredients of the sponge recipe are added to the McDuffee bowl of a Hobart mixer in the order listed. The ingredients are mixed for 1 minute using the No. 1 speed. The bowl is then scraped down and the sponge is again mixed for one minute at the No. 2 speed. The sponge is removed from the bowl at this point and transferred to a polyethylene bag and allowed to ferment at room temperature (~25°C.) for 4 four hours.

A sponge separately prepared as described in the above section is then placed in a 10 quart stainless-steel Hobart mixing bowl and the balance of the ingredients are added as outlined under the dough portion of the bread recipe. The mixture is mixed on No. 1 speed for 8 minutes. The resulting dough is then removed from the bowl and placed in a polyethylene bag and allowed to ferment for 24 minutes at room temperature (~25°C.). It is then scaled into 1 lb. portions, with at least four-1 lb. balls of dough being prepared for the subsequent testing. The balls are rounded (rolled into small balls by hand in order to exclude large air bubbles and gas pockets), and each ball is then run through the molder twice using a 5/16 inch setting for the first pass and 3/16 setting for the second. The molded dough is rolled into a cylinder approximately as long as the pan in which it is baked. The cylinder is tightened by placing in the automatic rollers to fit bread pan length between the ends. It is then dropped into greased bread pans, transferred to the proof box and proofed for one hour at 120°F. and 55% relative humidity. The proofed dough is baked at 43°F. for 25 minutes and the resulting bread allowed to cool for 1 hour. This bread contained the sodium cetyl succinate additive at the 0.270% concentration level, based on the total weight of the dough, which amounted to roughly 0.5% based on the flour. Three of the four bread loaves obtained are then packaged into polyethylene bags, and these packaged loaves are stored at room temperature and the compression data determined thereon at the end of 4, 5 and 6 days of storage time, respectively. Each of the unpackaged loaves, on the other hand, is sliced and compression data determinations are performed immediately thereon so as to provide "initial" data readings.

The compression determinations on each loaf are conducted on two-1 inch thick slices of bread, one slice being taken from the center of the bread and the other approximately one inch from the end. The compression test is performed with a standard penetrometer using a 1-inch diameter flat stainless-steel disc in place of the usual vaseline cone. A 150 g. weight is used as the load on the end of the compression disc. The load is placed on the slice for a period of five seconds, after which time the penetration is determined in tenths of millimeters. Three compressions are performed on each slice of bread, two in the bottom corners of the slice and the third at the top center. All data is recorded and the six values for each loaf are averaged. The results obtained in this manner at the concentration level tested (based on flour weight) are presented below in the following table, which also includes corresponding information on the monodiglyceride additive of commerce (Atmul 500), as well as a negative control (where there is no additive present) for comparison purposes:

| Additive | Compression Data (mm.$^{-1}$) | | | |
|---|---|---|---|---|
| | Initial | 4 | 5 | 6 Days |
| None (control) | 189 | 42 | 25 | 18 |
| Monodiglyceride[1] | 186 | 60 | — | 30 |
| Na cetyl succinate | 190 | 65 | 60 | 44 |

[1]Atmul 500, which is the registered trademark name of Atlas Chemical Industries for a mixture consisting of 65% monoglycerides and 35% diglycerides.

From the data presented in the above table, it can be seen that sodium cetyl succinate was found to be superior as a bread softening agent not only to the control, but also to the monodiglyceride of commerce as well.

EXAMPLE XLI

The procedure described in Example XL is followed employing in place of sodium cetyl succinate as the softening agent of choice any one of the other compounds reported in Example XXXV–XXXIX. In each and every case, the results obtained are substantially the same as those reported previously in the preceding example for sodium cetyl succinate.

Additionally, this same procedure is also repeated using the compounds of choice at different concentration levels other than that previously employed (which is 0.5%). For instance, when sodium cetyl succinate is employed at the 0.1% concentration level, based on the weight of the flour, the results obtained show that a bread softening effect is achieved in comparison with the control. In like manner, the use of sodium stearyl succinate at the 3.0% concentration level also affords a bread softening effect.

EXAMPLE XLII

The procedure described in Example XL was repeated as regards the preparation of the conventional sponge and dough formulation, including the added sodium cetyl succinate at the 0.5% concentration level, based on flour weight. However, in this particular case, the dough improver effects of the aforementioned succinate compound were investigated and breads were prepared using the optimum mixing time of 3¼ minutes, as well as severe overmix conditions of 7.5 minutes. Observations were then made on dough quality and on the quality of the finished goods, employing a negative control for comparison purposes. In these tests, three loaves of bread were baked for each test sample or control at a given mixing time for the dough (dough mixing time or DMT, in minutes), and the results obtained were thereafter averaged. The following table summarizes the representative data so obtained under these conditions, using a good quality bread cereal flour (⅓ Montana, ⅔ Kansas Spring - 65% absorption) for all the baking studies:

| Additive | DMT (min.) | Loaf Wt. (gm.) | Loaf Vol. (cc.) | Sp. Vol. cc./gm. | Bread Appearance & Dough Effects |
|---|---|---|---|---|---|
| None (control) | 3.25 | 397 | 2190 | 5.52 | Fair crumb, color and structure |
| Na cetyl succinate | 3.25 | 398 | 2140 | 5.38 | Good crumb, color and structure |
| None (control) | 7.5 | 405 | 2090 | 5.16 | Fair color, poor crumb and structure; dough v. sticky and runny at makeup |
| Na cetyl succinate | 7.5 | 402 | 2090 | 5.20 | Good color, fair crumb and structure; dough v. sl. sticky and runny at make-up |

From the above table, it is obvious that sodium cetyl succinate is consistently superior to the negative control, where there is no additive present, as regards both the grain and overall bread quality. Further, the dough produced on overmixing in the case of the instant cetyl succinate salt composition is stronger and substantially less sticky and runny in appearance on make-up.

EXAMPLE XLIII

The procedure described in Example XLII is repeated again using the other higher alkyl succinate salts reported previously in Examples XXXV – XXXIX. In each and every case, the results obtained show that the other compounds of this invention work substantially as well as dough improving agents when used in this manner as compared to the aforementioned sodium cetyl succinate.

Additionally, this same procedure is also employed using the compounds of choice at different concentration levels other than that previously mentioned (viz., 0.5%). For instance, when sodium stearyl succinate is employed at the 0.1% concentration level, based on flour weight, the results obtained show that a dough improving effect is achieved in comparison with the control. In like manner, the use of sodium cetyl succinate at the 3% concentration level also affords a dough improving effect.

EXAMPLE XLIV

A high-sugar white cake is pepared in the following manner from the ingredients listed below:

|  | Grams |
|---|---|
| Cake flour | 219 |
| Sugar | 291 |
| Baking powder[1] | 14 |
| Salt | 7 |
| Milk solids (non-fat) | 15.6 |
| Covo[2] | 100 |
| Egg whites | 113 |
| Water | 202 |

[1]Standard baking powder is used here, i.e., of the double action variety comprising corn starch, sodium bicarbonate, calcium acid phosphate and sodium aluminum sulfate.
[2]Covo is the registered trademark name of the Proctor & Gamble Co. for a plastic all-purpose vegetable shortening agent.

The first five ingredients in the above list are blended together for 3 minutes at the No. 1 speed in a Hobart Kitchenaid Mixer. This is then followed by the addition of the shortening, egg whites and water to the mix in one batch followed by the agitation of the whole at No. 2 speed for 1.5 minutes, stopping only after each half-minute to scrape down the bowl. THe batter is then checked for specific gravity and 425 grams of same is then scaled into an 8-inch round cake pan. The baking is done at 375°F. for twenty-six minutes.

This entire procedure is then repeated again using sodium cetyl succinate at both the 0.5% and 1% concentration levels, based on flour weight. The sodium cetyl succinate is dry-blended with the cake flour at the start of the procedure in each instance. The results obtained show that the treated cake samples, as in the case of bread, are consistently superior to the negative control, as regards both the firmness retarding effect and the dough improver qualities as well.

What is claimed is:

1. An improved potato composition adapted for reconstitution with water comprising dehyrated potato in comminuted form together with from about 0.1% to about 2% by weight, based on dried potato weight, of a substance selected from the group consisting of the sodium, potassium, calcium and magnesium salts of monoalkyl acid fumarates and maleates containing from 14 to 18 carbon atoms in the alkyl group.

2. A composition as claimed in claim 1 wherein the substance selected is sodium monostearyl fumarate.

3. A composition as claimed in claim 1 wherein the substance selected is calcium monostearyl fumarate.

4. A composition as claimed in claim 1 wherein the substance selected is sodium monocetyl fumarate.

5. A composition as claimed in claim 1 wherein the substance selected is sodium monostearyl maleate.

* * * * *